United States Patent [19]

Ghodsian

[11] Patent Number: 4,650,705
[45] Date of Patent: Mar. 17, 1987

[54] STERILE ADHESIVE SHEET

[76] Inventor: Kamran Ghodsian, 69 Woodward St., Roslyn Heights, N.Y. 11577

[21] Appl. No.: 828,131

[22] Filed: Feb. 10, 1986

[51] Int. Cl.⁴ .................... A61F 13/02; A61F 15/00; A61L 15/00
[52] U.S. Cl. ..................................... 428/40; 128/155; 128/156
[58] Field of Search .................. 128/156, 155; 428/40, 428/41, 42

[56] References Cited

U.S. PATENT DOCUMENTS 3,973,565  8/1976  Steer ................................ 128/214.4
3,978,266  8/1976  Lock ................................ 428/314.2

FOREIGN PATENT DOCUMENTS 0171557  9/1984  Japan.
540867  11/1941  United Kingdom.

Primary Examiner—John E. Kittle
Assistant Examiner—Patrick J. Ryan

[57] ABSTRACT

This invention relates to a new and improved design and composition for a sterile adhesive sheet designed for assisting in elevating the anterior abdominal wall of a patient during various surgical procedures wherein there is provided over one surface of the sterile adhesive sheet an adhesive material capable of affixing itself to the skin of a patient while having folds formed on the non-adhesive surface portion of said sterile adhesive sheet so as to provide for a means to grip said sterile adhesive sheet during a surgical procedure, thus enabling during a medical procedure the elevation of the anterior abdominal wall of a patient.

9 Claims, 5 Drawing Figures

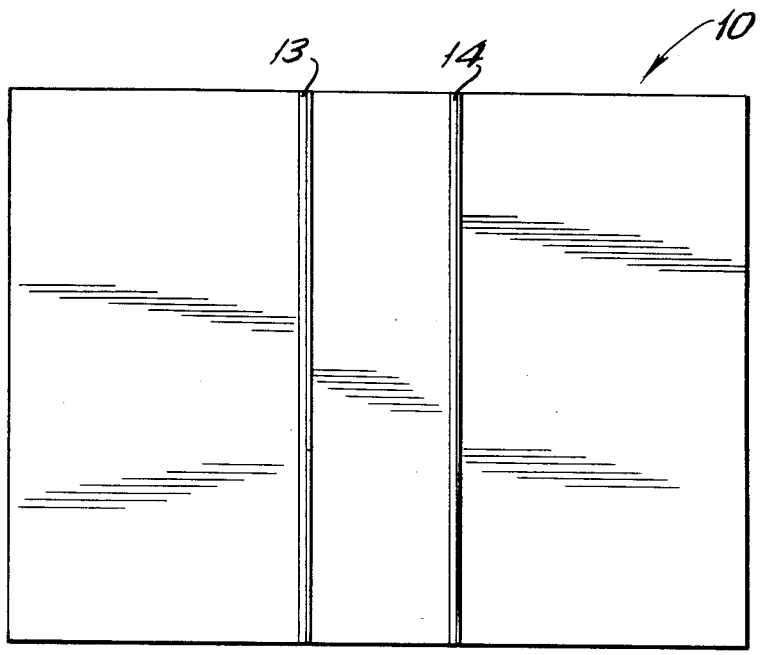
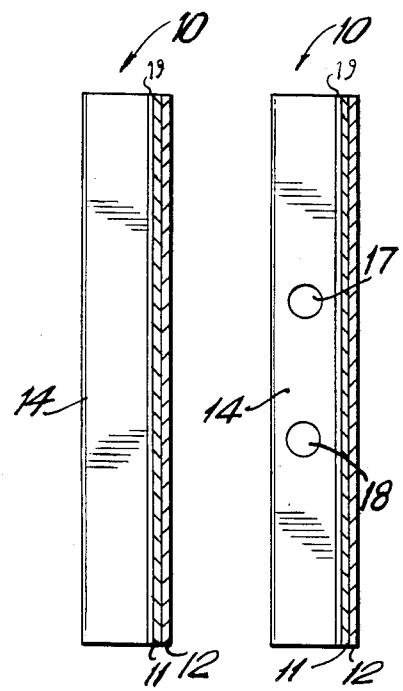
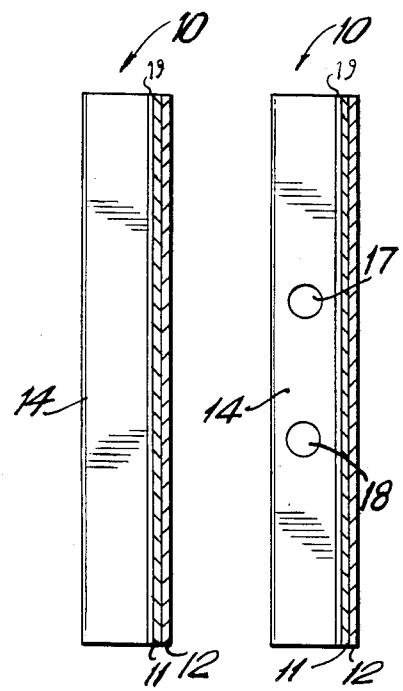
FIG. 1    FIG. 3    FIG. 5
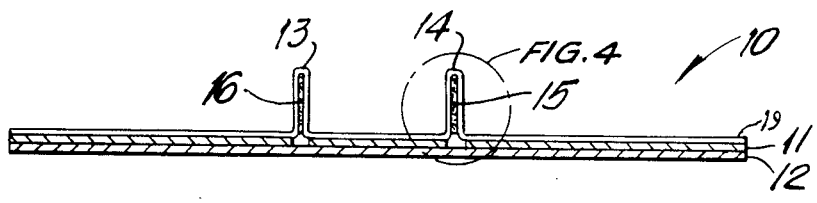
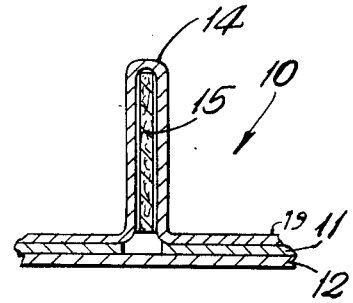
FIG. 2    FIG. 4

STERILE ADHESIVE SHEET

BACKGROUND AND OBJECTS OF THE INVENTION

With regard to present medical practice, there occurs a variety of situations and/or circumstances during which certain medical procedures need to be carried out wherein it becomes necessary to be able to elevate the anterior abdominal wall of a patient from the underlying internal organs positioned adjacent thereto. More particularly, such a technique is utilized during such procedures a Laparascopy, peritoneal tap, peritoneal lavage, as well as having applicability to various aspects of surgery, be it surgery of the abdominal area or not.

In the past, the method by which the anterior abdominal wall has been elevated away from the underlying abdominal organs during such procedures, techniques and/or surgery as referred to above has been by the utilization of various mechanical devices such as clamps and the like, all of which are cumbersome, cause additional morbidity to the area of utilization as well as necessitate extensive sterilization procedures before utilization. Additionally, the utilization of such clamps and the like necessitate additional personnel to be present during a procedure and/or operation simply for the purposes of assisting in the utilization thereof and to insure proper elevation of the abdominal wall.

It is in the context of the above that Applicant's present invention seeks to overcome many of the prior art disadvantages associated with said procedures and/or surgery that requires the lifting of the abdominal wall from its contact with other internal organs of the body and to otherwise provide a new and useful means and technique to accomplish same.

More particularly, it is an object of the invention to devise a new and improved design and composition for a sterile adhesive sheet which is capable of having one surface thereof adhesively adhere to the skin of a patient at a particular location on the patient's body and to have formed on the exposed non-adhesive surface thereof folds capable of providing to a surgeon a means to grab on to said sterile adhesive sheet so as to be able to lift the skin surface to which said sterile adhesive sheet is affixed in a fashion so as to able to lift the tissue in question away from the underlying body organs, same to be accomplished in a controlled and selected manner.

It is another object of the invention to create a new and improved design and composition for a sterile adhesive sheet wherein the folds formed adjacent to the exposed non-adhesive portion of said sheet additionally provide means for gripping of same by having formed therein openings which can be grasped by a surgeon's fingers.

It is another object of the invention to create a new and improved design and composition for a sterile adhesive sheet whereby said sterile adhesive sheet is capable of being cut and otherwise fashioned to any desired shape or form so as to be compatible with placement on any surface area of the human body without diminishing its capability of assisting in the lifting of surface tissue away from underlying organs of the body positioned at said location.

It is another object of the invention to create a new and improved design and composition for a sterile adhesive sheet capable of surgical application as referred to above whereby same is easily sterilized and inexpensive to fabricate such that same can be discarded after utilization without concern.

It is another object of the invention to create a new and improved design and composition for a sterile adhesive sheet wherein said sterile adhesive sheet is capable of being impregnated with antimicrobial agents so as to provide a means for decreasing the chances of infection at a particular location on the body where said sterile adhesive sheet is utilized in conjunction with a medical procedure or application.

It is another object of the invention to create a new and improved design and composition for a sterile adhesive sheet whereby said sterile adhesive sheet is also capable of providing the dual function of minimizing exposure to infection at a location of surgery upon the human body by having said sterile adhesive sheet also function as a surgical drape at said location.

SUMMARY OF THE INVENTION

This invention relates to a new and improved design and composition for a sterile adhesive sheet designed for assisting in the elevating of the anterior abdominal wall of a patient during various surgical procedures wherein there is provided over one surface of the sterile adhesive sheet an adhesive material capable of affixing itself to the skin of a patient while having folds formed on the non-adhesive surface portion of said sterile adhesive sheet so as to provide for a means to grip said sterile adhesive sheet during a surgical procedure so as to be able to elevate the anterior abdominal wall of a patient who has had said sterile adhesive sheet applied to the exterior portion thereof thus enabling the carrying out in a safe and prudent manner various surgical procedures.

BRIEF DESCRIPTION OF THE DRAWINGS

FIG. 1 is a top elevational view of a sterile adhesive sheet construction in accordance with the invention.

FIG. 2 is a front elevational view of the sterile adhesive sheet as depicted in FIG. 1.

FIG. 3 is a side elevational view of the sterile adhesive sheet as depicted in FIG. 1.

FIG. 4 is an enlarged partial elevational view of the sterile adhesive sheet depicted in FIG. 2 isolated at a point where a fold is formed.

FIG. 5 is an alternative embodiment of the sterile adhesive sheet as depicted in FIG. 3 wherein there is formed in said fold of said sterile adhesive sheet openings capable of permitting the insertion of a finger to enhance the gripping capability of said sterile adhesive sheet.

DESCRIPTION OF A PREFERRED EMBODIMENT

Reference is herein made to FIG. 1 of the drawings wherein there is depicted a top elevational view of sterile adhesive sheet 10 fabricated in accordance with the present invention.

More particularly, sterile adhesive layer 19 of sterile adhesive sheet 10 can be of any shape or size and fabricated from a variety of materials readily recognized and well known in the prior art for applications in surgical procedures and operations for dressings and the like, several examples of applicable material from which can be fashioned said sterile adhesive layer 19 of sterile adhesive sheet 10 are a sterile adhesive sheet made from polyethylene film, polyurethane film or a film of polyvinylchloride.

Although the above materials are cited for the purpose of setting forth the preferred composition from which sterile adhesive layer 19 of sterile adhesive sheet 10 is to be fabricated, nothing herein is to be interpreted to so limit the invention only to said materials, it being within the scope of this invention that any material capable of sterilization and capable of having placed upon a surface thereof an adhesive, is within the scope of this invention.

As depicted in FIG. 2 there is set forth a front elevational view of the sterile adhesive sheet 10 depicted in FIG. 1 wherein there is depicted adhesive material 11 affixed to the bottom surface of sterile adhesive layer 19 which has placed upon the exposed surface of adhesive material 11 a protective sheet 12 which prevents the inadvertent adherence of adhesive material 11 to an object other than that desired in accordance with appropriate medical procedures.

As depicted in FIG. 2, there is formed by overlapping portions of sterile adhesive layer 19, fold members 13 and 14, which have positioned along said respective folds, insert members 15 and 16 respectively. Insert members 15 and 16 can be fabricated from any one of a number of materials, it being the function of insert members 15 and 16 to provide additional strength and stability to fold members 13 and 14 respectively, so as to provide for a portion of said sterile adhesive sheet 10 to be capable of being firmly gripped by a surgeon utilizing said sterile adhesive sheet 10 during a particular medical procedure and to thus insure the ability of said surgeon to lift the surface of the patient's body to which said sterile adhesive sheet 10 has been affixed thereby separating it from underlying body organs in accordance with said medical procedure.

Although insert members 15 and 16 can be fabricated from any of a number of well known prior art materials, in the preferred embodiment set forth in the drawings, said insert members 15 and 16 are fashioned from either a film of polyethylene, a film of polyurethane or a film of polyvinylchloride.

FIG. 5 depicts an alternate embodiment of sterile adhesive sheet 10 as depicted in FIG. 1, FIG. 5 evidencing a side elevational view of sterile adhesive sheet 10 with having formed through fold members 13 and 14 respectively openings 17 and 18, said openings 17 and 18, also being formed through insert members 15 and 16 respectively so as to provide a through opening at each of said locations in fold members 13 and 14 respectively capable of permitting the insertion there through of a surgeon's finger or other medical instrument thus achieving mechanical assistance in the pulling up on sterile adhesive sheet 10. In this fashion there is provided a means to apply mechanical force to the abdominal wall or other portion of the human body to which said sterile adhesive sheet 10 has been applied with regard to a particular procedure so as to separate said abdominal wall, or the like, from underlying body tissue or organs.

Upon utilization of sterile adhesive sheet 10 in accordance with the invention, and as an example of its utilization with regard to an abdominal surgical procedure, upon a surgeon making an incision through a patient's abdominal wall, sterile adhesive sheet 10 is applied adjacent to said incision upon the abdomen of said patient either immediately prior thereto or immediately thereafter, same being affixed by initially removing protective sheet 12, thus exposing adhesive material 11 of sterile adhesive sheet 10, and in a fashion well known in medical practice, adhesive material 11 of sterile adhesive sheet 10 is caused to come into contact with the appropriate abdominal area of the patient.

In this fashion, there is now affixed sterile adhesive sheet 10 to the abdominal wall of a patient and upon the surgeon or someone assisting the surgeon gripping either fold member 13 and/or 14 or both fold members 13 and 14 simultaneously, there is achieved the ability to mechanically pull away said abdominal wall from the underlying body tissue and/or body organs so as to permit carrying forth of a particular surgical procedure without further morbidity occurring with regard to said abdominal wall or surrounding tissue.

Additionally, it should be noted that it is within the scope of this invention to have adhesive sheet 10 act as an antiseptic drape about portions of a patient's body at the point where an incision has been made during the surgical process in addition to having adhesive sheet 10 utilized as a means to manipulate said patient's abdominal wall. Furthermore, it is also within the scope of this invention to have impregnated within the structure of adhesive sheet 10 antimicrobial agents so as to decrease chances of infection occurring at the point of incision.

Although the above example addresses itself to a medical procedure related to the incision in the abdominal wall of a patient, its utilization in accordance with the invention has applicability to anyone of a number of medical procedures and/or operations that require the control of a patient's surface tissue in the fashion as described above.

I claim:

1. A sterile adhesive sheet comprising;
   (a) a sterile adhesive layer formed to provide a fold member across the top surface thereof;
   (b) adhesive material affixed to the bottom surface of said adhesive layer;
   (c) a protective sheet sized to coincide with the area of said sterile adhesive layer that has affixed thereto said adhesive material, said protective sheet being placed over and in direct contact with said adhesive material and being capable of selective removal from said adhesive material.

2. A sterile adhesive sheet as described in claim 1 wherein said sterile layer is fabricated from a film of polyethylene.

3. A sterile adhesive sheet as described in claim 1 wherein said sterile layer is fabricated from a film of polyurethane.

4. A sterile adhesive sheet as described in claim 1 wherein said sterile layer is fabricated from a film of polyvinylchloride.

5. A sterile adhesive sheet as described in claim 1 wherein the said sterile adhesive layer is impregnated with antimicrobial agents.

6. A sterile adhesive sheet as described in claim 1 wherein the fold member formed across the top surface of said sterile adhesive layer has formed there through an opening so as to provide mechanical leverage in grasping said sterile adhesive sheet.

7. A sterile adhesive sheet as described in claim 1 wherein the fold member formed across the top surface of said sterile adhesive layer has formed there through several openings so as to provide mechanical leverage in grasping said sterile adhesive sheet.

8. A sterile adhesive sheet as described in claim 1 wherein said sterile adhesive layer has formed a pair of fold members across the top surface thereof.

9. A sterile adhesive sheet as described in claim 1 wherein said fold member has contained therein an additional layer of sterile adhesive material so as to provide structural strength thereto.

* * * * *